(12) United States Patent
O'Brien et al.

(10) Patent No.: US 11,181,552 B2
(45) Date of Patent: Nov. 23, 2021

(54) CATEGORIZATION OF ACQUIRED DATA BASED ON EXPLICIT AND IMPLICIT MEANS

(71) Applicant: Tektronix, Inc., Beaverton, OR (US)

(72) Inventors: Joshua J. O'Brien, Aloha, OR (US); Brian S. Mantel, Tigard, OR (US)

(73) Assignee: Tektronix, Inc., Beaverton, OR (US)

(*) Notice: Subject to any disclaimer, the term of this patent is extended or adjusted under 35 U.S.C. 154(b) by 52 days.

(21) Appl. No.: 16/695,795

(22) Filed: Nov. 26, 2019

(65) Prior Publication Data

US 2020/0166546 A1    May 28, 2020

Related U.S. Application Data

(60) Provisional application No. 62/772,480, filed on Nov. 28, 2018.

(51) Int. Cl.
  *G01R 13/02* (2006.01)
  *G01R 13/22* (2006.01)
  *G06N 3/04* (2006.01)
(52) U.S. Cl.
  CPC .......... *G01R 13/029* (2013.01); *G06N 3/04* (2013.01); *G01R 13/02* (2013.01); *G01R 13/0254* (2013.01)
(58) Field of Classification Search
  CPC .. G01R 13/029; G01R 13/0254; G01R 13/02; G06N 3/04
  (Continued)

(56) References Cited

U.S. PATENT DOCUMENTS 3,504,164 A * 3/1970 Lachenmayer .... G06K 9/00536
  702/73
4,560,981 A * 12/1985 Jackson ............... G06F 11/322
  345/440.1
(Continued)

FOREIGN PATENT DOCUMENTS

EP    0433626    6/1991
EP    3096152    11/2016
WO   2018119316   6/2018

OTHER PUBLICATIONS

European Patent Office, International Search Report and Written Opinion for International Application No. PCT/US2019/063497, dated Mar. 2, 2020, 13 pages, Rijswijk, NL.

*Primary Examiner* — Ly D Pham
(74) *Attorney, Agent, or Firm* — Miller Nash LLP; Andrew J. Harrington

(57) ABSTRACT

A method of classifying waveform data includes receiving input waveform data at a test and measurement system, accessing a repository of reference waveform data and corresponding classes, analyzing the input waveform data and the reference waveform data to designate a class of the input waveform data, and using the class designation to provide information to a user. A test and measurement system has a user interface, at least one input port, a communications port, a processor, the processor configured to execute instructions causing the processor to: receive input waveform data through at least one of the input port or the user interface; access a repository of reference waveform data; analyze the input waveform data using the reference waveform data; designate a class of the input waveform data; and use the class to provide information to the user about the input waveform.

18 Claims, 3 Drawing Sheets

(58) Field of Classification Search
USPC .................................................... 702/66, 67
See application file for complete search history.

(56) References Cited

U.S. PATENT DOCUMENTS

| | | | | |
|---|---|---|---|---|
| 5,517,105 | A * | 5/1996 | Holzwarth | G01R 13/30 |
| | | | | 324/121 R |
| 7,359,810 | B2 * | 4/2008 | Letts | G01R 13/029 |
| | | | | 345/440.1 |
| 8,055,464 | B2 * | 11/2011 | Rule | G01R 13/029 |
| | | | | 702/68 |
| 9,294,237 | B2 * | 3/2016 | Guenther | H04L 1/205 |
| 10,379,141 | B2 * | 8/2019 | Deverson | G01R 13/0254 |
| 10,585,121 | B2 * | 3/2020 | Absher | G01R 13/02 |
| 2012/0021710 | A1 * | 1/2012 | Tsukamoto | H04B 17/327 |
| | | | | 455/226.1 |
| 2014/0059098 | A1 * | 2/2014 | Otani | G06K 9/6203 |
| | | | | 708/209 |
| 2016/0341766 | A1 * | 11/2016 | Deverson | G01R 13/029 |

* cited by examiner

CATEGORIZATION OF ACQUIRED DATA BASED ON EXPLICIT AND IMPLICIT MEANS

RELATED APPLICATIONS

This application is a continuation of, and claims priority to, U.S. Provisional Patent Application No. 62/772,480, filed Nov. 28, 2018.

FIELD

This disclosure relates to data acquisition in test and measurement systems, more particularly to ways to categorize the data acquired.

BACKGROUND

Users of test and measurement instruments, for example, oscilloscopes, expect their instruments to be smart and enable them to work faster by configuring settings automatically or recommending options that may be useful. Test and measurement systems that acquire or receive user data can automatically setup measurements, derivative data, heuristic analysis, and data views, if the system can correctly categorize the data.

Data can be characterized by explicit or implicit means if the system provides the capability. However, manually developing methods to characterize data by implicit factors is burdensome.

Embodiments of the disclosed apparatus and methods address shortcomings in the prior art.

DETAILED DESCRIPTION

The embodiments here provide users the ability to categorize data explicitly, or to have a system that can implicitly categorize data collected by test and measurement systems. Data can be categorized by explicit and/or implicit means. A user may explicitly categorize the data by creating measurements on the data. As an example, a user creates a jitter measurement on a signal. This action indicates that the signal is very likely to be a clock or high speed serial data. If the user also creates a jitter measurement that is based on inter symbol interference, the system can conclude that the data is not a clock. Other applications like power analysis and bus decodes inform the system of the category of data.

A system can also be designed to look for implicit characteristics of the data without user intervention. If a user creates a derivative waveform of one waveform subtracted from another waveform than the system can infer that the waveforms are a differential signal. However, even without the user creating the differential waveform, the system could compare both waveforms and mathematically determine that they are a differential waveform.

As users employ explicit methods to categorize or classify data, the data and the determined classes can be stored. These classes can become labels in the data. With enough labeled data, machine-learning algorithms can find the implicit characteristics of new data. This will remove the burden of developing these algorithms, and likely find relationships and implicit characteristics that are not obvious to developers.

The embodiments here allow the users to classify the data directly or as feedback to the system that stores the classes with the waveform data. When the system operates, it stores the waveforms with associated data, often referred to as metadata, and provides a classification or category for the waveform. This allows the test and measurement device to search waveforms of that same class to access the metadata for previous configurations and/or tests and use information from those for the current session.

As used here, the term "waveform data" means the actual waveform and the associated data. The term "waveform" means the waveform generated by the instrument in either image or raw data format. Similarly, "input waveform data" means the input waveform initially generated by the user, and "reference waveform data" means the waveforms and their associated data stored in a repository.

The embodiments here will generally include test and measurement instruments, such as oscilloscopes, digital multi-meters, source measurement units, etc. While some of these instruments may perform one or the other of testing and measuring, the term "test and measurement instrument" applies to both or any of these instruments. The term "system" includes the instrument and any other parts of the embodiments here, such as a network and a repository.

Figure 1:
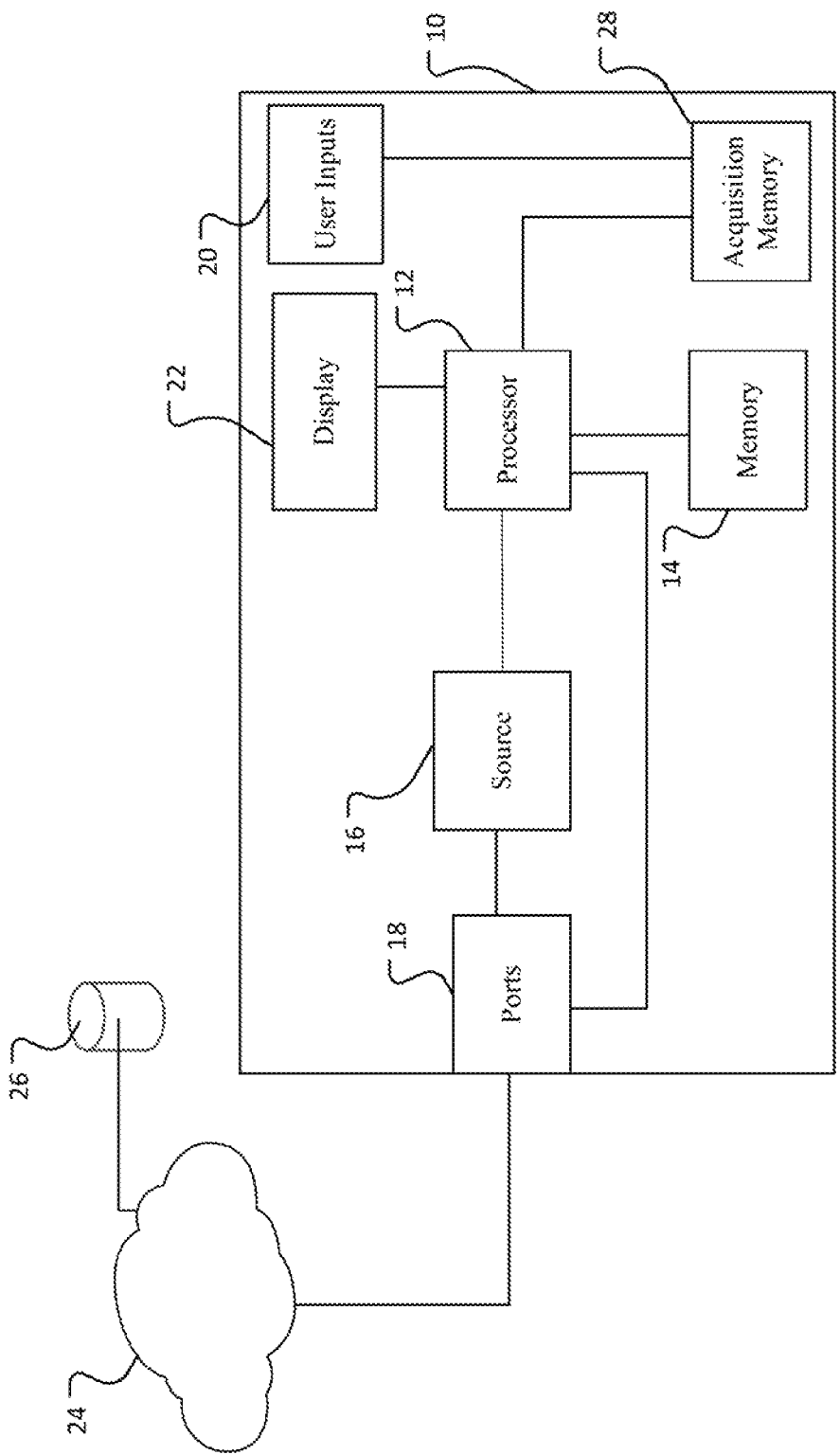
FIG. 1 shows an embodiment of a test and measurement system.

FIG. 1 shows an embodiment of a test and measurement system that employs categories or classes of the data collected. Using classes, the instrument can provide information to the user with regard to test set up configurations, instrument settings, quality of data, etc. The test and measurement instrument 10 of FIG. 1 has at least one processor 12 and a memory 14. The memory 14 may store data, the instructions for the processor to execute that cause the instrument to operate, and the repository. In the embodiment of FIG. 1, the repository 26 resides remote from the instrument 10. The repository contains waveform or waveforms and their metadata. These may include training sets, discussed in more detail below, or collected waveform data or a mix of the two.

Typically, the repository will start at or grow to a rather extensive size, so more than likely the repository will reside remote to the test and measurement instrument. However, the test and measurement instrument could store the repository or at least part of it, such as the waveform data generated upon that instrument. The repository may gather waveform data from more than just one instrument. It could contain data from all instruments of a certain type, or all instruments in total. With security concerns that may arise with the repository residing remotely, such as in a network cloud like 24, the repository may only contain data generated from a particular customer's instruments, etc. The configuration of the repository and its contents has no limits, nor do limits exist as to its architecture.

The instrument 10 communicates with the repository through the ports 18. In addition to these ports, user inputs 20 may include connectors and connections related to the testing probes or other types of testing and/or measurement accessories used in the instrument's operation. An acquisition memory 28 will store these inputs, with the user inputs connected to the acquisition memory and the acquisition memory 28 connected to the processor 12. The instrument may contain a source 16, such as a voltage or current source, used in testing. The instrument may also contain a user interface that allows the user to interact with the instrument. The combination of the user inputs 20 and the display 22 represents an example of a user interface. As will be discussed in more detail later, the instrument may provide selections of test configurations and settings, as well as proposed classes of data for received waveforms for which the user may provide feedback. The user interface will allow accomplishment of these tasks.

Figure 2:
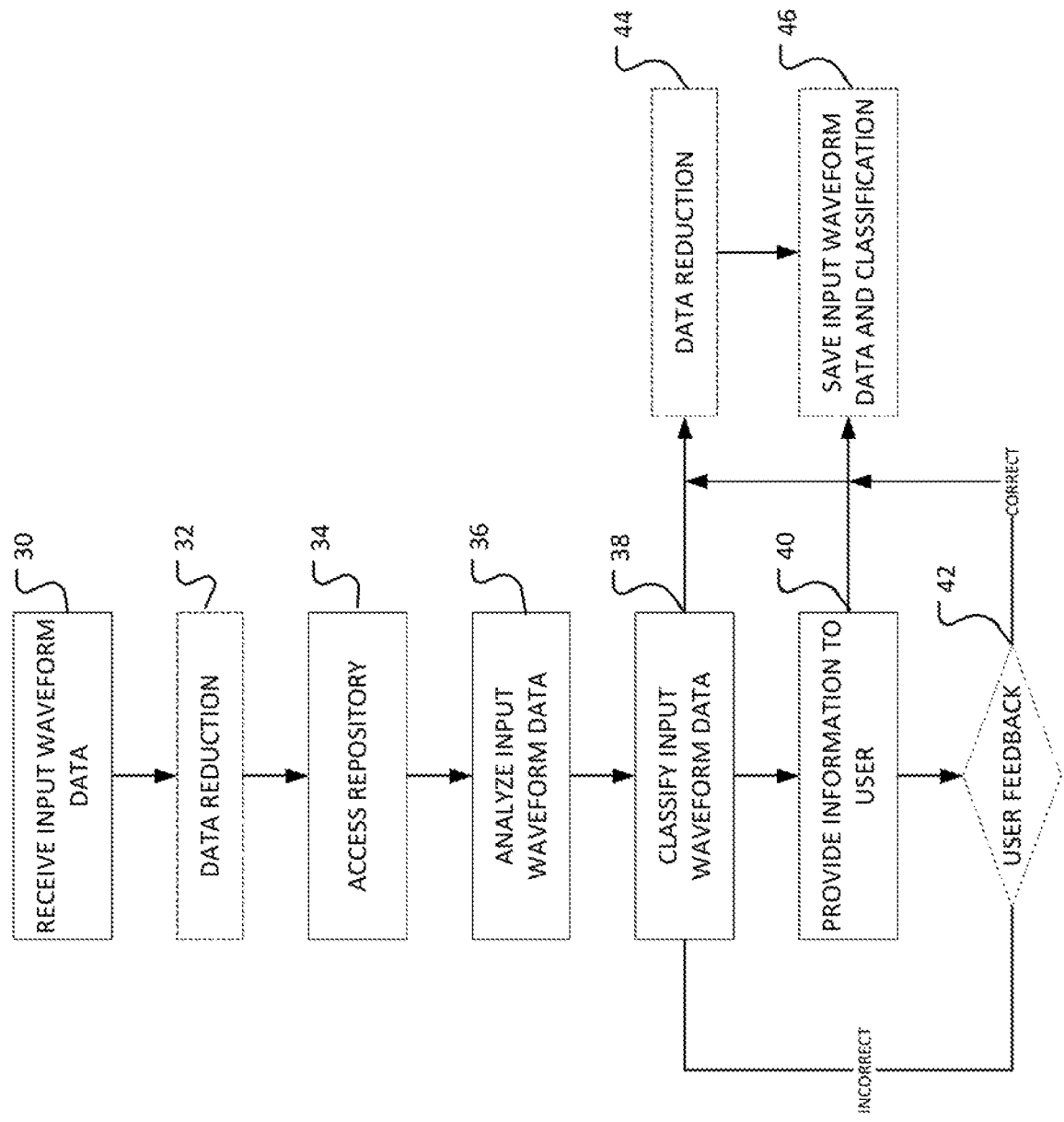
FIG. 2 shows a flowchart of an embodiment of a method to use a test and measurement system that classifies waveform data.

FIG. 2 shows an embodiment of a user employing an instrument such as the one in FIG. 1. When the user uses the instrument and captures a waveform, the instrument receives it at 30. The instrument may store the waveform at this point. If so, the process may perform data reduction or filtering techniques to reduce the amount of data requiring storage at 32. These may include such techniques such as removal of redundant data, missing value ratio analysis, low variance filters, high correlation filters, principal component analysis, backward feature elimination, and forward feature construction. In the flowchart of FIG. 2, the optional processes have dashed lines.

The input waveform data may include the waveform in either image or raw waveform data, or any conversions or other derivations from the waveform. In addition, data accompanies the waveform, referred to as associated data or metadata. This data may include settings on the instrument, configuration data, type of probe used, any source signals, etc.

At 34, the processor of the instrument accesses the repository of reference waveform data. The processor may comprise a general-purpose processor or may comprise part of an artificial neural network, such as a convolutional neural network, deep neural network or other deep learning processing entity. The term "neural network" as used here refers to an artificial neural network. A convolutional neural network (CNN) employs convolution, a mathematical operation instead of general matrix multiplication. CNNs have particular affinities for image analysis. In deep neural networks, each operation occurs in a different layer, with multiple layers between the input and output. These are examples of machine learning methods using artificial neural networks, typically made up of a network of simple processing elements. The processor referred to here as being part of the instrument may be one of those elements, or may provide access to the neural network.

Using either a deep learning network or a general-purpose processor, the instrument analyzes the waveform data at 36. The analysis may comprise comparing the input waveform to other input waveforms. The analysis results in classification of the input waveform at 38. The classification may take many forms. Generally, the classes represent signals that fit given instrument set-ups, such as switching power supplies, EMI (electromagnetic interference), WiFi, serial data, etc. The classes used, and therefore the classification process, may be generic or specific, depending upon the user preference or strength of the classification. If a class gives a strong correlation to a specific signal type, the process would employ that class for the signal.

If a general-purpose processor performs the data analysis, the analysis may take the form of statistical data analysis, pattern recognition, or time-series mining, among many others.

In another embodiment, the classes have more than one level. For example, the process can perform a first classification to assign a waveform a first class, and then use a more specific sub-class within that first class. This process can iterate as many times as needed to refine the classification.

Once the process determines a class for the input waveform at 38, the process provides information to the user at 40. The information may not actually reach the user directly, but the process could perform a pre-defined or user-defined set up for the instrument. It could also use the auto-set features of instruments to configure the instrument. For example, the process could enable a Fast Fourier Transform (FFT) of the input waveform and adjust the span appropriately for the signal, such as a WiFi or radio signal. A further regression analysis would allow further insight into signal attributes, such as the width of the RF spectrum, that could then apply or adjust settings in the measurement equipment.

In addition to the set up and configuration aspect of the information provided to the user, the process could also provide information about the data to the user based upon the class. The process could compare the input waveform to other waveforms in the class to determine if the waveform has captured a problem in the user's system. Generally, outside of data captured using rigorous compliance methods, test and measurement instruments do not have a good way to report whether data is within specification or compliance. This process could determine if data statistically falls within the norm for data from other waveforms in the same class, i.e. "good" data, or whether the data falls far outside the other waveforms, i.e. "bad" data. This may involve applying heuristic methods. This process could indicate what aspect of the waveform is outside of the norm to the user.

Once the input waveform data undergoes classification, the process could provide for user feedback at 42. For example, the system may inform the user, through the user interface, that the process "thinks" that the input waveform data indicates a differential signal being analyzed. If a neural network makes that determination, it may weight that determination with other possible outcomes and presents the top determinations and the network's percentage of confidence. The user could then select the actual signal undergoing analysis. If the process made an incorrect determination, the process may return to the classification at 38 and update its training set or make an error adjustment, etc. If the process made a correct determination, the process may save the class and the waveform at 46. The process may save the waveform data and resulting class at this point or earlier in the process. As mentioned previously, prior to saving the process may perform data reduction such as at 44 after determining the class.

Figure 3:
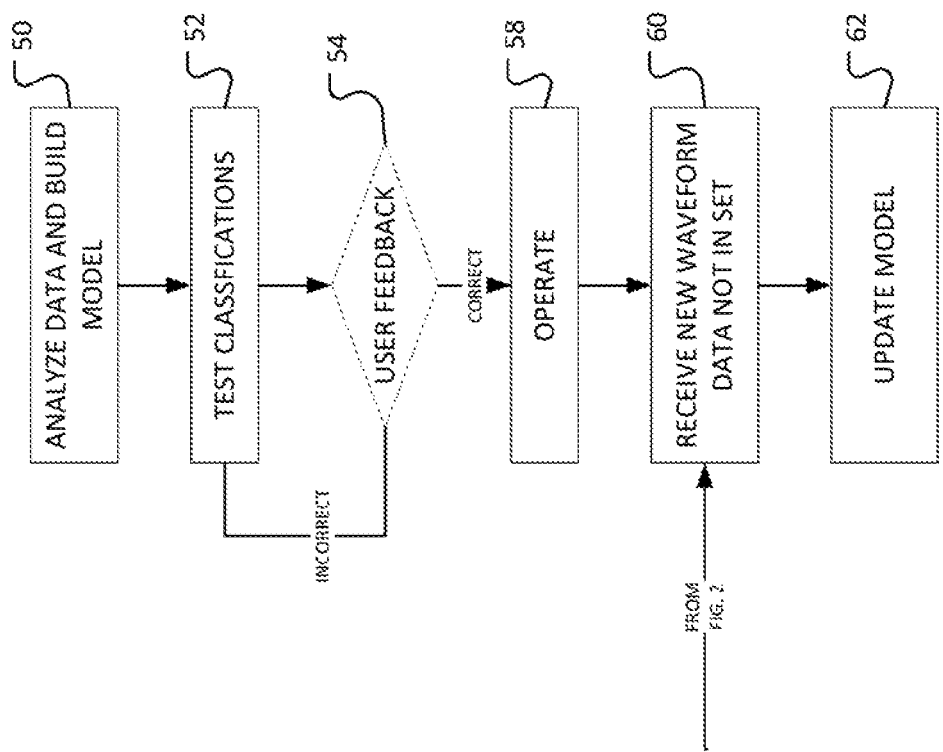
FIG. 3 shows a flowchart of an embodiment of a method to train a test and measurement system to classify waveform data automatically.

If the waveform and its associated data is "new" to the process, the process may also update the training set used for the neural network if used. The machine learning techniques, including the deep neural network or convolutional neural network, depend upon a robust training set to "teach" the network to make the proper classification of the input waveform data. FIG. 3 shows one embodiment of such a process.

Generally, neural networks use a training set to perform pattern recognition and build one or more models to allow them to break down and analyze the data. This occurs in FIG. 3 at 50. Once the network/processor completes the training by consuming the training set, the process may test the accuracy of the network by testing the classifications at 52. The training sets may result from actual user data, or could be internally generated. One possible approach includes providing user feedback at 54 as to the correctness of the classification, similar to that performed during system operation. Once the network/processor has sufficient accuracy, the system operates. Periodic updates to the training set may occur, including when the user provides a previously unseen input waveform data as mentioned in FIG. 2, at 60. The process then updates the model(s) to include the new data with the previous data at 62. The new data may result in a shift in the pattern recognition, or may provide data for a "hole" in the model that previously did not have data.

In this manner, a test and measurement instrument can become "smarter" and provide more automation and consistency in testing procedures without overburdening the users to develop this automation.

In this disclosure, the singular forms "a," "an," and "the" include plural referents unless the context dictates otherwise. The term "or" is meant to be inclusive and means either, any, several, or all of the listed items. The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. Relative terms, such as "about," "approximately," "substantially," and "generally," are used to indicate a possible variation of ±10% of a stated or understood value.

The aspects of the present disclosure are susceptible to various modifications and alternative forms. Specific aspects have been shown by way of example in the drawings and are described in detail herein. However, one should note that the examples disclosed herein are presented for the purposes of clarity of discussion and are not intended to limit the scope of the general concepts disclosed to the specific aspects described herein unless expressly limited. As such, the present disclosure is intended to cover all modifications, equivalents, and alternatives of the described aspects in light of the attached drawings and claims.

References in the specification to aspect, example, etc., indicate that the described item may include a particular feature, structure, or characteristic. However, every disclosed aspect may or may not necessarily include that particular feature, structure, or characteristic. Moreover, such phrases are not necessarily referring to the same aspect unless specifically noted. Further, when the discussion described a particular feature, structure, or characteristic in connection with a particular aspect, such feature, structure, or characteristic can be employed in connection with another disclosed aspect whether or not such feature is explicitly described in conjunction with such other disclosed aspect.

Aspects of the disclosure may operate on a particularly created hardware, on firmware, digital signal processors, or on a specially programmed general-purpose computer including a processor operating according to programmed instructions. The terms controller or processor as used herein include microprocessors, microcomputers, Application Specific Integrated Circuits (ASICs), cloud-based servers, and dedicated hardware controllers. One or more aspects of the disclosure may be embodied in computer-usable data and computer-executable instructions, such as in one or more program modules, executed by one or more computers (including monitoring modules), or other devices. Generally, program modules include routines, programs, objects, components, data structures, etc. that perform particular tasks or implement particular abstract data types when executed by a processor in a computer or other device. The computer executable instructions may be stored on a non-transitory computer readable medium such as a hard disk, optical disk, removable storage media, solid-state memory, Random Access Memory (RAM), etc. As will be appreciated by one of skill in the art, the functionality of the program modules may be combined or distributed as desired in various aspects. In addition, the functionality may exist in whole or in part in firmware or hardware equivalents such as integrated circuits, FPGA, and the like. Particular data structures may be used to implement more effectively one or more aspects of the disclosure, and such data structures are contemplated within the scope of computer executable instructions and computer-usable data described herein.

The disclosed aspects may be implemented, in some cases, in hardware, firmware, software, or any combination thereof. The disclosed aspects may also be implemented as instructions carried by or stored on one or more or non-transitory computer-readable media, which may be read and executed by one or more processors. Such instructions may be referred to as a computer program product. Computer-readable media, as discussed herein, means any media that accessible by a computing device. By way of example, and not limitation, computer-readable media may comprise computer storage media and communication media.

Computer storage media means any medium that can store computer-readable information. By way of example, and not limitation, computer storage media may include RAM, ROM, Electrically Erasable Programmable Read-Only Memory (EEPROM), flash memory or other memory technology, Compact Disc Read Only Memory (CD-ROM), Digital Video Disc (DVD), or other optical disk storage, magnetic cassettes, magnetic tape, magnetic disk storage or other magnetic storage devices, and any other volatile or nonvolatile, removable or non-removable media implemented in any technology. Computer storage media excludes signals per se and transitory forms of signal transmission.

Communication media means any media that can communicate computer-readable information. By way of example, and not limitation, communication media may include coaxial cables, fiber-optic cables, air, or any other media suitable for the communication of electrical, optical, Radio Frequency (RF), infrared, acoustic or other types of signals.

Further, when this application refers to a method having two or more defined steps or operations, the defined steps or operations can be carried out in any order or simultaneously, unless the context excludes those possibilities, such as a first step depending upon the results of another step.

EXAMPLES

Illustrative examples of the disclosed technologies are provided below. An embodiment of the technologies may include one or more, and any combination of, the examples described below.

Example 1 is a method of classifying waveform data, comprising: receiving input waveform data at a test and measurement system; accessing a repository of reference waveform data and corresponding classes; analyzing the input waveform data and the reference waveform data to designate a class of the input waveform data; and using the class designation to provide information to a user.

Example 2 is the method of Example 1, wherein the input waveform data includes an input waveform and metadata associated with the input waveform.

Example 3 is the method of Example 2, wherein the metadata includes at least one of: settings for the test and measurement system; probes used to receive the input waveform data; ranges of output Example 4 is the method of any one of Examples 1-3, wherein analyzing the input waveform data comprises one of using a convolutional neural network, using a deep neural network, or performing data analysis.

Example 5 is the method of Example 4, wherein performing data analysis comprises performing at least one of statistical data analysis, pattern recognition, and time series mining.

Example 6 is the method of any one of Examples 1-5, wherein designating the class comprises providing a first class based on a signal type of the input waveform data and then providing a second class from within first class.

Example 7 is the method of any one of Examples 1-6, wherein using the class designation to provide information to the user comprises applying a pre-defined set up to the test and measurement system.

Example 8 is the method of any one of Examples 1-7, wherein using the classification to provide information to the user comprises providing the designated class to the user to allow the user to confirm the class.

Example 9 is the method of any one of Examples 1-8, wherein using the class designation to provide information to the user comprises providing a comparison of the input waveform to other waveforms in a same class as the input waveform.

Example 10 is the method of any one of Examples 1-9, further comprising training a processor in the test and measurement system using at least one training set of the reference waveform data and corresponding classes.

Example 11 is the method of Example 10, wherein the training set comprises a training set acquired from user data.

Example 12 is the method of either Example 10 or 11, further comprising saving the input waveform data and associated class to the repository as training data.

Example 13 is the method of any one of Examples 1-12, further comprising applying at least one of data reduction and filtering to the input waveform data.

Example 14 is a test and measurement system, comprising: a user interface; at least one input port; a communications port; a processor, the processor configured to execute instructions causing the processor to: receive input waveform data through at least one of the input port or the user interface; access a repository of reference waveform data; analyze the input waveform data using the reference waveform data; designate a class of the input waveform data; and use the class to provide information to the user about the input waveform.

Example 15 is the system of Example 14, wherein the user interface includes at least one display screen to allow the system to display the proposed configuration.

Example 16 is the system of either one of Examples 14 or 15, wherein the repository resides local to the test and measurement system.

Example 17 is the system of any one of Examples 14-16, wherein the repository resides remotely from the test and measurement system.

Example 18 is the system of Example 17, wherein the repository is accessible through the communications port.

Example 19 is the system of any one of Examples 14-18, wherein the processor is part of, or has access to, a convolutional neural network or a deep neural network.

Example 20 is the system of any one of Examples 14-19, wherein the processor is further configured to execute instructions that cause the processor to designate a first class based on a signal type of the input waveform, and to designate a second class that is a sub-class of the first class.

Although specific embodiments have been illustrated and described for purposes of illustration, it will be understood that various modifications may be made without departing from the spirit and scope of the disclosure. Accordingly, the invention should not be limited except as by the appended claims.

The invention claimed is:

1. A method of classifying waveform data, comprising:
receiving input waveform data at a test and measurement system;
applying at least one of data reduction and filtering to the input waveform data;
accessing a repository of reference waveform data and corresponding classes;
analyzing the input waveform data and the reference waveform data to designate a class of the input waveform data; and
using the class designation to provide information to a user.

2. The method as claimed in claim 1, wherein the input waveform data includes an input waveform and metadata associated with the input waveform.

3. The method as claimed in claim 2, wherein the metadata includes at least one of: settings for the test and measurement system; probes used to receive the input waveform data; ranges of output.

4. The method as claimed in claim 1, wherein analyzing the input waveform data comprises one of using a convolutional neural network, using a deep neural network, or performing data analysis.

5. The method as claimed in claim 4, wherein performing data analysis comprises performing at least one of statistical data analysis, pattern recognition, and time series mining.

6. The method as claimed in claim 1, wherein designating the class comprises providing a first class based on a signal type of the input waveform data and then providing a second class from within first class.

7. The method as claimed in claim 1, wherein using the class designation to provide information to the user comprises applying a pre-defined set up to the test and measurement system.

8. The method as claimed in claim 1, wherein using the class designation to provide information to the user comprises providing the designated class to the user to allow the user to confirm the class.

9. The method as claimed in claim 1, wherein using the class designation to provide information to the user comprises providing a comparison of the input waveform to other waveforms in a same class as the input waveform.

10. The method as claimed in claim 1, further comprising training a processor in the test and measurement system using at least one training set of the reference waveform data and corresponding classes.

11. The method as claimed in claim 10, wherein the training set comprises a training set acquired from user data.

12. The method as claimed in claim 10, further comprising saving the input waveform data and associated class to the repository as training data.

13. A test and measurement system, comprising:
a user interface;
at least one input port;
a communications port;
a processor, the processor being part of, or having access to, a convolutional neural network or a deep neural network, the processor configured to execute instructions causing the processor to:

receive input waveform data through at least one of the input port or the user interface;

access a repository of reference waveform data;

analyze the input waveform data using the reference waveform data;

designate a class of the input waveform data; and use the class to provide information to the user about the input waveform.

14. The system as claimed in claim 13, wherein the user interface includes at least one display screen to allow the system to display the proposed configuration.

15. The system as claimed in claim 13, wherein the repository resides local to the test and measurement system.

16. The system as claimed in claim 13, wherein the repository resides remotely from the test and measurement system.

17. The system as claimed in claim 16, wherein the repository is accessible through the communications port.

18. The system as claimed in claim 13, wherein the processor is further configured to execute instructions that cause the processor to designate a first class based on a signal type of the input waveform, and to designate a second class that is a sub-class of the first class.

* * * * *